US 11,010,843 B2

(12) United States Patent
Heywood et al.

(10) Patent No.: US 11,010,843 B2
(45) Date of Patent: *May 18, 2021

(54) SYSTEMS AND METHODS FOR ENCOURAGEMENT OF DATA SUBMISSION IN ONLINE COMMUNITIES

(71) Applicant: PatientsLikeMe, Inc., Cambridge, MA (US)

(72) Inventors: James Heywood, Newton Highlands, MA (US); Paul Wicks, Wokingham (GB)

(73) Assignee: PatientsLikeMe, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/521,300

(22) Filed: Jul. 24, 2019

(65) Prior Publication Data
US 2019/0347744 A1    Nov. 14, 2019

Related U.S. Application Data

(63) Continuation of application No. 15/418,348, filed on Jan. 27, 2017, now Pat. No. 10,402,916, which is a
(Continued)

(51) Int. Cl.
G06Q 50/00    (2012.01)
G06Q 10/00    (2012.01)
(Continued)

(52) U.S. Cl.
CPC .............. G06Q 50/01 (2013.01); G06Q 10/00 (2013.01); G06Q 10/10 (2013.01); G06Q 30/02 (2013.01);
(Continued)

(58) Field of Classification Search
CPC .............................. G06Q 50/22; G06Q 50/24
(Continued)

(56) References Cited

U.S. PATENT DOCUMENTS 6,529,195 B1   3/2003  Eberlein
6,856,315 B2   2/2005  Eberlein
(Continued)

FOREIGN PATENT DOCUMENTS

JP    2001175761 A    6/2001
JP    2002539561 A   11/2002
(Continued)

OTHER PUBLICATIONS

Office Action for Canadian Patent Application No. 2,758,481, dated Oct. 11, 2016.
(Continued)

Primary Examiner — Barbara B Anyan
(74) Attorney, Agent, or Firm — Greenberg Traurig, LLP; David J. Dykeman; Kristopher Reichlen

(57) ABSTRACT

The invention relates to systems and methods for behavioral modification of users in an online community where users store or share data to help one another reach informed decisions. One aspect of the invention provides a method for encouraging active participation in an online community. The method includes: receiving information from a first user regarding a topic, receiving a request from a second user for additional information desired from the first user, and sending a personalized message to the first user requesting the additional information. Another aspect of the invention provides a computer-readable medium whose contents cause a computer to perform a method for encouraging active participation in an online community. The method includes: receiving information from a first user regarding a topic; identifying additional information desired from the first
(Continued)

user; and sending a personalized message to the first user requesting the additional information.

19 Claims, 6 Drawing Sheets

Related U.S. Application Data continuation of application No. 13/223,969, filed on Sep. 1, 2011, now Pat. No. 9,589,251, which is a continuation of application No. PCT/US2010/001226, filed on Apr. 26, 2010.

(60) Provisional application No. 61/174,189, filed on Apr. 30, 2009.

(51) Int. Cl.
   *G06Q 30/02* (2012.01)
   *G06Q 10/10* (2012.01)
   *G04F 7/06* (2006.01)
   *G06F 15/16* (2006.01)
   *G06F 3/00* (2006.01)

(52) U.S. Cl.
   CPC .............. *G04F 7/06* (2013.01); *G06F 3/00* (2013.01); *G06F 15/16* (2013.01); *Y02A 90/10* (2018.01)

(58) Field of Classification Search
   USPC ....... 709/203, 204, 205, 206, 217, 219, 223, 709/224
   See application file for complete search history.

(56) References Cited

U.S. PATENT DOCUMENTS

| | | | |
|---|---|---|---|
| 8,160,901 | B2 | 4/2012 | Heywood et al. |
| 8,643,648 | B2 | 2/2014 | Heywood et al. |
| 8,930,224 | B2 | 1/2015 | Heywood et al. |
| 9,270,632 | B2 | 2/2016 | Heywood et al. |
| 9,589,104 | B2 | 3/2017 | Heywood et al. |
| 9,589,251 | B2 | 3/2017 | Heywood et al. |
| 10,402,916 | B2 | 9/2019 | Heywood et al. |
| 10,665,344 | B2 | 5/2020 | Heywood et al. |
| 10,832,816 | B2 | 11/2020 | Heywood et al. |
| 2002/0177757 | A1 | 11/2002 | Britton |
| 2002/0184094 | A1 | 12/2002 | Calloway |
| 2005/0102162 | A1 | 5/2005 | Blumenfeld |
| 2005/0187866 | A1* | 8/2005 | Lee ................................ 705/39 |
| 2006/0059160 | A1* | 3/2006 | Smola et al. ................. 707/10 |
| 2007/0061487 | A1 | 3/2007 | Moore et al. |
| 2007/0168461 | A1 | 7/2007 | Moore |
| 2007/0168501 | A1 | 7/2007 | Cobb et al. |
| 2007/0177757 | A1 | 8/2007 | Funahashi et al. |
| 2007/0288266 | A1 | 12/2007 | Sysko et al. |
| 2008/0077489 | A1 | 3/2008 | Gilley et al. |
| 2008/0109412 | A1 | 5/2008 | Drayer et al. |
| 2008/0133716 | A1 | 6/2008 | Rao et al. |
| 2008/0229213 | A1* | 9/2008 | Hamilton et al. ............ 715/751 |
| 2008/0238666 | A1 | 10/2008 | Loncar |
| 2008/0312510 | A1 | 12/2008 | Ross |
| 2008/0313256 | A1 | 12/2008 | Kanazawa et al. |
| 2009/0018862 | A1 | 1/2009 | Sanger et al. |
| 2009/0037470 | A1 | 2/2009 | Schmidt |
| 2009/0048865 | A1 | 2/2009 | Breazeale, Jr. |
| 2009/0144089 | A1 | 6/2009 | Heywood et al. |
| 2009/0172773 | A1 | 7/2009 | Moore |
| 2009/0222284 | A1 | 9/2009 | McEachern |
| 2009/0234755 | A1 | 9/2009 | Sidoruk |
| 2010/0131860 | A1* | 5/2010 | DeHaan et al. .............. 715/751 |
| 2011/0029895 | A1 | 2/2011 | Ternouth |
| 2011/0184747 | A1 | 7/2011 | Bozic et al. |
| 2017/0206327 | A1 | 7/2017 | Heywood et al. |
| 2020/0279622 | A1 | 9/2020 | Heywood et al. |

FOREIGN PATENT DOCUMENTS

| | | |
|---|---|---|
| JP | 2003256573 A | 9/2003 |
| JP | 2004178264 A | 6/2004 |
| JP | 2005038055 A | 2/2005 |
| JP | 2007140905 A | 6/2007 |
| JP | 2008513884 A | 5/2008 |
| JP | 2008177713 A | 7/2008 |
| JP | 2010500648 A | 1/2010 |
| JP | 2011501276 A | 1/2011 |
| JP | 2011501845 A | 1/2011 |
| WO | WO-2008/089084 A2 | 7/2008 |
| WO | 2009049277 A1 | 4/2009 |
| WO | WO-2009/049278 A1 | 4/2009 |
| WO | WO-2010/126577 A1 | 11/2010 |

OTHER PUBLICATIONS

International Search Report and Written Opinion for International Application No. PCT/US2010/001226, dated Jun. 25, 2010.

International Preliminary Report on Patentability for International Application No. PCT/US2010/001226, dated Nov. 1, 2011.

Banerjee, N. et al., "R-U-In? : Doing What You Like, with People Whom You Like", WWW 2008, 1239-1240. Apr. 21-25, 2008. Beijing, China.

Beenen, G., et al., "Using Social Psychology to Motivate Contributions to Online Communities", CSCW '04. Nov. 6-10, 2004. Chicago, Illinois.

Cosley, D., et al., "SuggestBot: Using Intelligent Task Routing to Help People Find Work in Wikipedia", IUI '07, Jan. 28-31, 2007, Honolulu, Hawaii. 32-41.

Frankowski, D., et al., "Recommenders Everywhere: The WikiLens Community-Maintained Recommender System", WikiSym '07, Oct. 21-23, 2007 Montreal, Quebec, Canada. 47-59.

Frost et al., "Social Uses of Personal Health Information Within PatientsLikeMe", Medicine 2.0: Social Networking and Web 2.0 Applications in Medicine and Health, Toronto, Canada, Sep. 4-5, 2008.

Geyer, W., et al., "Recommending Topics for Self-Descriptions in Online User Profiles", RecSys '08, Oct. 23-25, 2008, Lausanne, Switzerland. 59-66.

Harper, F.M., et al., "Talk Amongst Yourselves: Inviting Users to Participate in Online Conversations", IUI '07, Jan. 28-31, 2007, Honolulu, Hawaii. 62-71.

Iriberri, A., et al., "A Life-Cycle Perspective on Online Community Success", ACM Computing Surveys, 41, 2, Article 11. Feb. 2009.

Koh, J., et al., "Encouraging Participating in Virtual Communities", Communications of the ACM, Col. 50, No. 2. Feb. 2007. 69-73.

Liu et al., "Towards a Rich-Context Participatory Cyberenvironment", International Workshops on Grid Computing Environments 2007, Nov. 11-12, 2007, Reno, Nevada.

Nielsen, J., "Participation Inequality: Encouraging More Users to Contribute", Participation Inequality in Social Design. Oct. 2006.

Rashid, A.M., et al., "Motivating Participating by Displaying the Value of Contribution", CHI 2006, Apr. 22-27, 2006, Montreal Quebec, Canada. 955-58.

\* cited by examiner

Nudge: User DataJunkie wants to say thank you

Dear BlessedWithMS,

Thank you for entering in your data in response to my nudge for more data. In the past week, 20 users have read the Prozac report of whom 5 (25%) said it helped them make a decision about their treatment. By adding your data to the Prozac report you have helped our community and patients like me and you to make better decisions.

Thank you again!

DataJunkie

502

Dosages
Based on the
patients currently
taking Fluoxetine.

| 43 | 9 | 2 | 6 | 26 | 1 | 7 | 4 | 1 |

10 mg daily, 20 mg daily, 25 mg daily, 30 mg daily, 40 mg daily, 50 mg daily, 60 mg daily, 80 mg daily, 200 mg daily Your data The Prozac report contains data from 300 patients, your data represents 0.33% of the total. You are taking the second most common dose of Prozac.

In the past week, 20 users read this report, 5 users (25%) said it helped them make a treatment decision since you added your data

Fluoxetine

Brand Names: Actan, Karib Kemi, Lovan, Prozac
Generic Name: Fluoxetine

What is Fluoxetine? Fluoxetine hydrochloride is an antidepressant drug used medically in the treatment of depression, body dysmorphic disorder, obsessive-compulsive disorder, bulimia nervosa, anorexia nervosa, premenstrual dysphoric disorder, hypochondriasis and panic disorder. Read more...

See more information, including instructions, precautions, side effects, and interactions.

➔ Jump to: Reasons Taken | Dosages | Duration

Reasons Taken
131 patients in the community are taking or have taken Fluoxetine.

| Reason | Count | % |
|---|---|---|
| Depression | 77 | 58% |
| Other | 29 | 22% |
| Fatigue | 7 | 5% |
| Mood swings | 4 | 3% |
| Emotional lability | 4 | 3% |
| General health | 4 | 3% |
| Pain | 2 | 1% |
| Anxiety | 1 | <1% |
| Slow my MS progress | 1 | <1% |
| Stiffness/spasticity | 1 | <1% |

Dosages
Based on the patients currently taking Fluoxetine.

| Dose | Count |
|---|---|
| 10 mg daily | 9 |
| 20 mg daily | 43 |
| 25 mg daily | 2 |
| 30 mg daily | 6 |
| 40 mg daily | 26 |
| 50 mg daily | 1 |
| 60 mg daily | 7 |
| 80 mg daily | 4 |
| 200 mg daily | 1 |

✉ ShareThis

▦ I'm taking Fluoxetine
Prozac (fluoxetine)
Update this treatment
⚠ Report new Adverse Event ☆ ☆
Click here if this treatment report helped you make a decision about your treatment!
☆ ☆

👥 Patients

Taking Fluoxetine user14661
Prozac, 10mg daily since Aug 01, 2000 user15943
Prozac, 20mg daily since Apr 15, 2008 user10332
40mg daily since Jan 27, 2000

👤 113 Patients currently take Fluoxetine
👤 18 Patients stopped taking Fluoxetine

FIG. 6

SYSTEMS AND METHODS FOR ENCOURAGEMENT OF DATA SUBMISSION IN ONLINE COMMUNITIES

RELATED APPLICATIONS

This application is a continuation under 35 U.S.C. § 120 of International Application No. PCT/US10/01226, filed on Apr. 26, 2010, which claims priority to U.S. Provisional Patent Application Ser. No. 61/174,189, filed on Apr. 30, 2009. The entire contents of these applications are hereby incorporated by reference herein.

TECHNICAL FIELD

The invention relates to systems and methods for behavioral modification of users in an online community where users store or share data to help one another reach informed decisions. Embodiments of invention are particularly applicable to interactive forums such as message boards or other online communities.

BACKGROUND OF THE INVENTION

The advent of the World Wide Web offers new opportunities for people to share information, opinions, and experiences on virtually any topic. With the support of web-based systems and methodologies, people with common goals and interests can interact and communicate instantaneously from anywhere on the globe.

Many web sites exist to serve a particular group of people who share common goals or attributes. Key to these activities is the sharing of data, whether quantitative or qualitative, in order to harness the wisdom of crowds to reach sound decisions.

Conventional interactive forums suffer from the fact that only a small subset of users contribute their data (e.g., numerical data such as salaries or qualitative data such as hotel reviews), which can potentially lead to bias and limit the ability of a user to draw valid conclusions from the shared dataset. Research suggests that participation in data-sharing platforms such as YOUTUBE®, WIKIPEDIA®, or PATIENTSLIKEME® is a more exaggerated form of the Pareto Principle, wherein 80% of data is contributed by 20% of users. This phenomenon has been referred to as "participation inequality". Although robust statistics are not available, it has been estimated by many leaders in the field that a tiny proportion of users (approximately 1-5%) account for product reviews, article edits, blog posts, forum posts, and the like.

Accordingly, there is a need for systems and methods for encouraging of data submission in online communities.

SUMMARY OF THE INVENTION

The invention relates to systems and methods for behavioral modification of users in an online community where users store or share data to help one another reach informed decisions.

One aspect of the invention provides a method for encouraging active participation in an online community. The method includes: receiving information from a first user regarding a topic, receiving a request from a second user for additional information desired from the first user, and sending a personalized message to the first user requesting the additional information.

This aspect can have a variety of embodiments. The method can include receiving the additional information from the first user. The method can include updating a database with the additional information. The personalized message can include a component generated by the second user. The method can include notifying the second user when the additional information is received. The method can include prompting the second user to thank the first user.

The online community can be a topic-related online community. The topic can relate to health. The additional data can include at least one medical condition metric. The medical condition metric can be a quantitative representation of a medical condition. The medical condition metric can be one selected from the group consisting of: a direct measure of pathology, a user-reported measure of functional impairment, a user-reported outcome of health-related quality of life, and a user-reported progression of a medical condition.

The medical condition can be one selected from the group consisting of: movement disorders including parkinsonism, Huntington's chorea, and Tourette's syndrome; pain disorders including back pain; rheumatologic disorders including arthritis, osteoarthritis, rheumatoid arthritis, psoriatic arthritis, Lyme's disease, and gout; seizure disorders including epilepsy; neurodegenerative diseases including amyotrophic lateral sclerosis, multiple sclerosis, Creutzfeld-Jakob disease, and Alzheimer's disease; pulmonary diseases including asthma, chronic obstructive pulmonary disease, and cystic fibrosis; sexual disorders including erectile dysfunction and vaginismus; mood disorders including depression and anxiety; addiction including nicotine addiction and alcoholism; migraines; fibromyalgia; fatigue disorders; dementia; eating disorders; hypercholesterolemia; hyperlipidemia; hyperlipoproteinemia; hypertriglyceridemia; vasculatitis, diabetes; obesity; gastroesophogeal reflux disorder; dyspepsia; anemia; cancer; hypertension; renal failure; lupus; and pregnancy.

The relevant data can include intervention data. The intervention data can include at least one selected from the group consisting of: intervention dosage, intervention frequency, intervention adherence, and perceived intervention efficacy. The invention data can be data about an intervention selected from the group consisting of: administration of a medication, administration of a remedy, administration of a nutritional supplement, administration of a vitamin, exercise, physical therapy, massage, stretching, consumption of food, rest, and sleep. The method can be a computer-implemented method.

The method can include providing an interface for the first user to the additional data. The method can include displaying the additional data along pre-existing data report. The method can include displaying hyperlinks to additional information about a subject of the personalized message along with the personalized message. The first user or the second user can be pre-identified.

The relevant data can include one or more adverse events. Adverse events can include one or more selected from the group consisting of side effects, hospitalizations, and monies paid. The relevant data includes one or more selected from the group consisting of laboratory data, general qualitative data, and diagnostic test data.

The method can be a computer-implemented method.

Another aspect of the invention provides a computer-readable medium whose contents cause a computer to perform a method for encouraging active participation in an online community. The method includes: receiving information from a first user regarding a topic; identifying additional information desired from the first user; and sending a personalized message to the first user requesting the additional information.

The computer-readable medium can be non-transitory and tangible.

Another aspect of the invention provides a system for encouraging active participation in an online community. The system includes: a server configured to receive information from a first user regarding a topic, identify additional information desired from the first user, and send a personalized message to the first user requesting the additional information; and a first client configured to transmit information from the first user to the server and receive a personalized message from the server.

This aspect can have a variety of embodiments. The system can include a second client configured to transmit a request for the additional information to the server and receive a notification that the additional information was provided by the first user.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views and wherein:

FIG. 5 depicts an acknowledgment message according to an embodiment of the invention.

FIG. 6 depicts a report according to an embodiment of the invention.

DEFINITIONS

The instant invention is most clearly understood with reference to the following definitions:

As used in the specification and claims, the singular form "a," "an," and "the" include plural references unless the context clearly dictates otherwise.

The term "nudge" refers to a private message, email, graphic, sound file, text message (SMS), or other form of transmitted data that serves as a specific request from one peer ("peer nudger") to another peer ("nudgee") to share a specific piece of data in order to help the community make better decisions.

The term "disease" refers to an abnormal condition of an organism that impairs bodily functions. The term disease includes a variety of physical ailments including, but not limited to, neurological diseases (e.g., Amyotrophic Lateral Sclerosis (ALS), Multiple Sclerosis (MS), Parkinson's Disease), Human Immunodeficiency Virus (HIV), Acquired Immune Deficiency Syndrome (AIDS), cancers (e.g., bladder cancer, blood cancer, breast cancer, colorectal cancer, endometrial cancer, leukemia, lung cancer, lymphoma, ovarian cancer, pancreatic cancer, prostate cancer, and skin cancer), diabetes, digestive disorders (e.g., irritable bower syndrome, gastro esophageal reflux disease, and Crohn's Disease), cardiovascular diseases, osteoporosis, chronic obstructive pulmonary disease (COPD), arthritis, allergies, geriatric diseases, and autoimmune diseases (e.g., lupus). The term disease also include mental ailments including, but not limited to, depression, anxiety disorders, post traumatic stress disorder, mood disorders, psychotic disorders, personality disorders, and eating disorders.

The term "medical condition" refers to a manifestation of a disease such as a symptom. For example, if a patient suffers from Amyotrophic Lateral Sclerosis (ALS), the patient may experience one or more medical conditions such as dysphagia (impaired swallowing).

The term "intervention" refers any event that has a positive, negative, or neutral effect on one or more medical conditions. The term intervention includes a variety of activities including, but not limited to, administration of a medication, administration of a remedy, administration of a nutritional supplement, administration of a vitamin, exercise, physical therapy, massage, stretching, consumption of food, rest, and sleep.

DETAILED DESCRIPTION

Various aspects of the invention described herein provide systems and methods for behavioral modification of users in an online community. Aspects of the invention are particularly applicable to interactive forums such as message boards (also known as Internet forums, online discussion sites, bulletin boards. Aspects of the invention are also applicable to other varieties of Internet applications.

Figure 1:
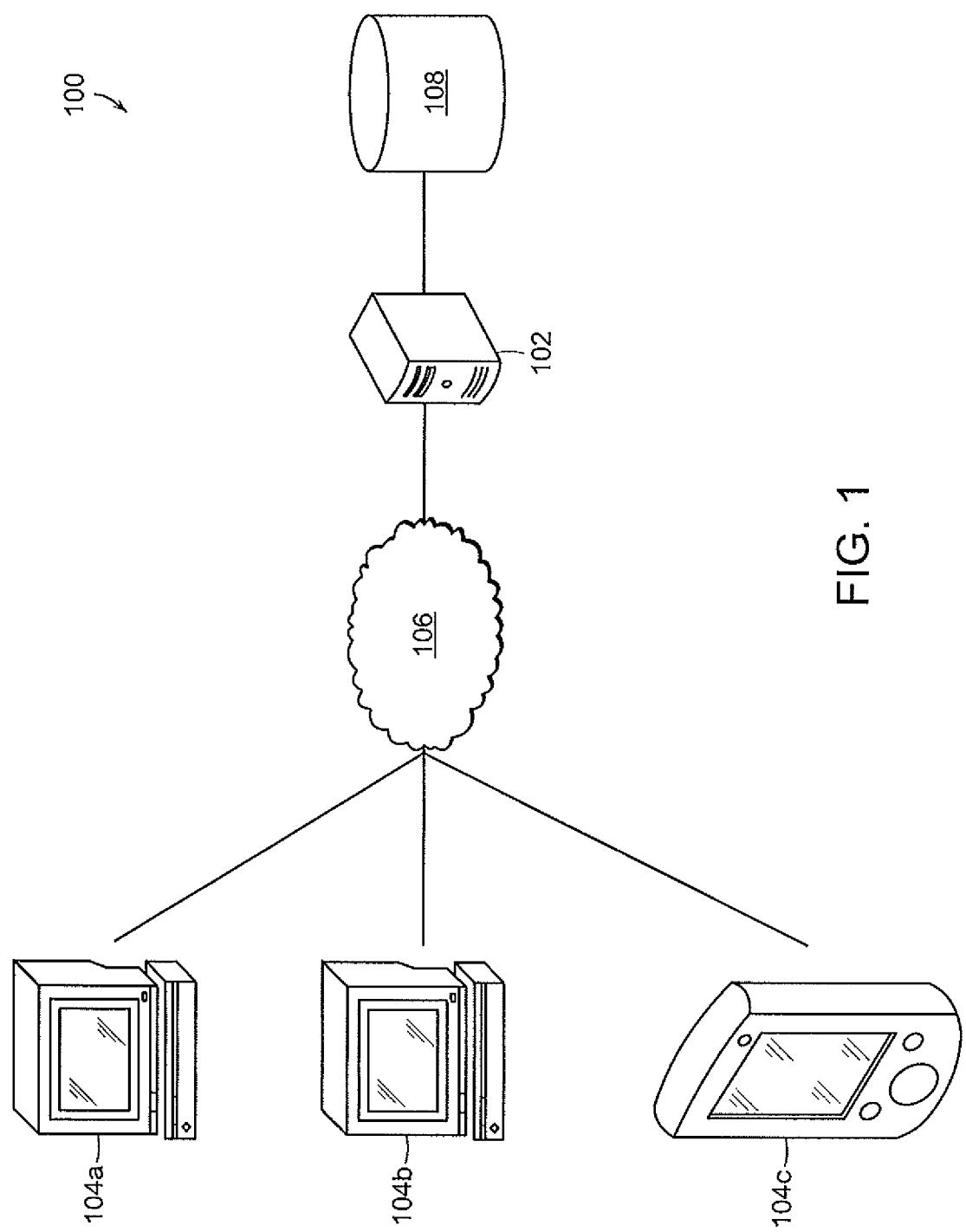
FIG. 1 depicts an exemplary network topology according to an embodiment of the invention.

Referring to FIG. 1, an exemplary network topology 100 for an interactive forum (e.g., a message board) is depicted. The message board is hosted on server 102, which is in communication with clients 104a-c via network 106.

The terms "client" and "server" are used to reflect a client-server relationship between elements 102 and 104a-104c. Suitable devices for server element 102 include, but are not limited to general-purpose computers, including, but not limited to computers with higher processing power colloquially known as "servers." Likewise, suitable devices for client elements 104a-104c include, but are not limited to general-purpose computers, including, but not limited to desktop computers, laptop computers, personal digital assistants, cellular telephones, smartphones, video game systems, digital video recorders (DVRs), and the like.

Network 106 can be any network capable of transmitting data between clients 104a-104c and server 102, for example, an intranet or the Internet.

The server can be in communication with a database 108. Database 108 can be operated through a database management system (DBMS). A DBMS is imposed upon the data to form a logical and structured organization of the data. A DBMS lies between the physical storage of data and the users and handles the interaction between the two. Examples of DBMSes include DB2® and INFORMIX®, both available from IBM Corp. of Armonk, N.Y.; MICROSOFT JET® and MICROSOFT SQL SERVER®, both available from the Microsoft Corp. of Redmond, Wash.; MYSQL®, available from the MySQL Ltd. Co. of Stockholm, Sweden; ORACLE® Database, available from Oracle Int'l Corp of Redwood City, Calif.; and SYBASE®, available from Sybase, Inc. of Dublin, Calif.

Various embodiments of the invention facilitate increased participation in online communities. Online communities are manifold in the modern networked world. For example, an online community can be focused on a particular topic, such as one or more diseases. Such communities include the PATIENTSLIKEME® system, available from Patients-LikeMe, Inc. of Cambridge, Mass. Other online communities can be focused on online games (e.g., WORLD OF WARCRAFT®), television shows, home improvement, cooking, and the like.

A powerful aspect of online communities is the ability to obtain information and/or advice from a wider variety of individuals than may exist in the user's physical network. However, research and experience suggests that this potential is not fully exploited. Accordingly, the invention provides systems and methods for encouraging the submission of user information to online communities.

Figure 2:
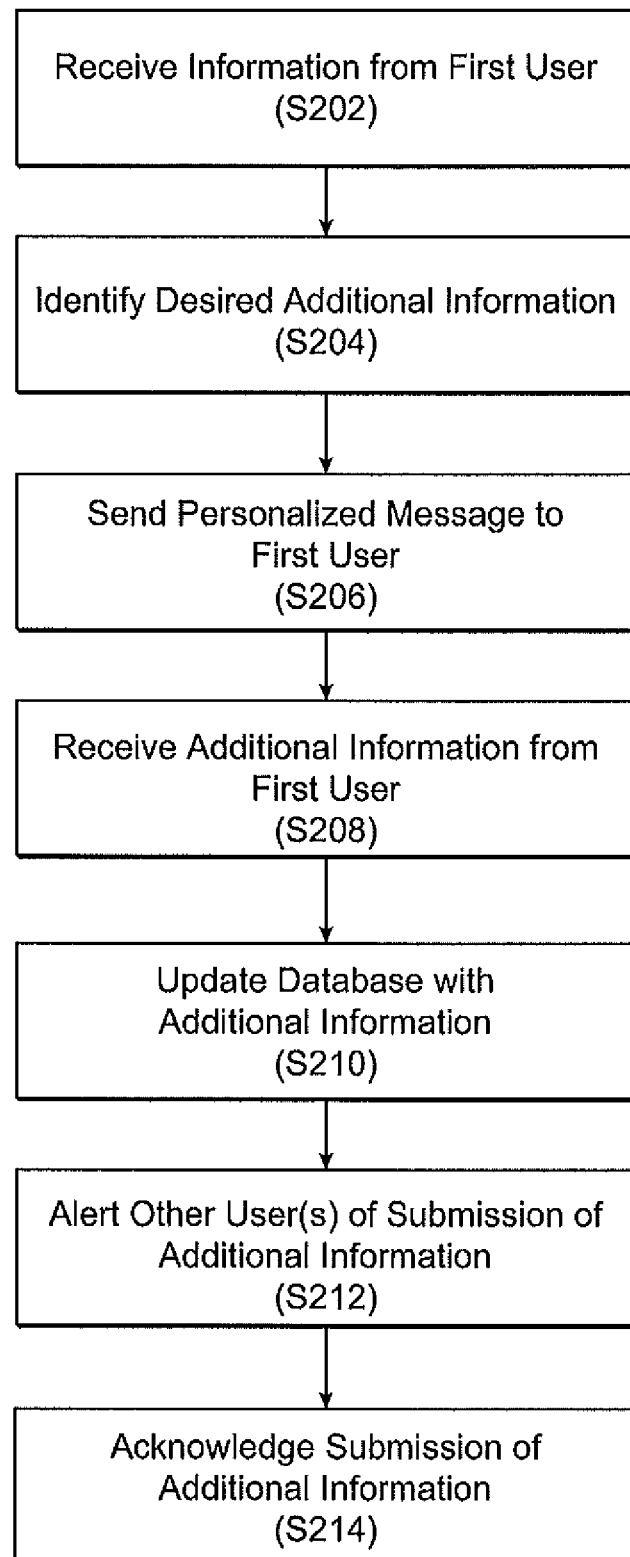
FIG. 2 depicts a method for encouraging active participation in an online community according to an embodiment of the invention.

FIG. 2 depicts a method 200 for encouraging active participation in an online community. In step S202, information is received from a first user. The information will often concern a particular topic. For example, in a health-related online community, the first user may create a profile indicating that he suffers from multiple sclerosis (MS) and is currently taking COPAXONE® (glatiramer acetate). However, the user may initially enter incomplete information or the user's participation in the online community may wane as the user fails to provide frequent updates on his adherence to the COPAXONE® regimen and his MS symptoms.

In step S204, desired additional information is identified. This additional information is in many embodiments of particular interest and/or relevance to one or more other users of the online community. For example, the first user may be one of ten 25 year old males diagnosed with MS at age 20. As such, the first user's progression of MS and experience COPAXONE® may be particularly relevant to a second user that is 20 years old and newly diagnosed with MS.

Relevant additional information can be identified in several ways. In one embodiment, a data mining process or module examines existing data to determine what additional information might be of interest to the second user. For example, the system may analyze data to determine what additional information would be helpful to creating a prediction for a nudger. The system can then automatically send request on behalf of the nudger. In another embodiment, the nudger can browse and/or search data associated with other users of the online community and, upon finding other users of interest, request additional information. In a third embodiment, a hybrid approach is employed wherein data for one or more users is presented for the nudger's review. For example, the system may present profiles for 10 users having MS and similar demographic information to the nudger. The nudger can then request additional information from one or more users whose profiles were presented.

In step S206, a personalized message is sent to the first user asking the first user to provide the additional information to the online community. The personalized message can be addressed specifically to the first user, or the first user may be one of a small group of users. In some embodiments, the personalized message includes a component provided by the second user.

Personalized messages promote increased user submission of information. The nudgee may be more inclined to provide information due to a desire to help the specifically identified nudger.

The personalized message be presented in a variety of media and transmitted through a variety of means as appreciated by those of skill in the art. For example, the personalized message can include one or more text, audio, video, and/or graphics components. The personalized message can be presented to the first user upon login to the online community or transmitted to the first user by email, Short Message Service (SMS), instant messaging, telephone, postal service, and the like.

In step S208, the additional information is received from the first user. In step S210, this additional information can be integrated into the online community, for example by storing the additional information in a database. The additional information is then available to other users and for processing by the online community.

In step S212, one or more other users are alerted of the submission of the additional information by the first user. This alert can be presented in a variety of media and transmitted through a variety of means as appreciated by those of skill in the art and discussed herein in the context of the personalized message in S206. In some embodiments, the nudger is alerted. In other embodiments, other users that may benefit from the submitted data are alerted. Users can configure alert settings to receive updates on a periodic basis. For example, a user can receive daily or weekly updates on which users posted data requested by the user and/or requested by other users, but relevant to the user.

In step S214, an acknowledgement is sent to the first user. This acknowledgment can be presented in a variety of media and transmitted through a variety of means as appreciated by those of skill in the art and discussed herein in the context of the personalized message in S206. In some embodiments, the acknowledgment includes a component generated by the second user. In other embodiments, the acknowledgment is automatically generated.

The inventions herein are further explained through the following examples, which are intended to further illustrate certain embodiments, but not to limit the invention in any way.

Example 1

Health-Related Online Community

Figure 3:
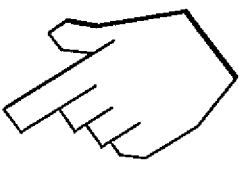
FIG. 3 depicts an excerpt from a user profile in an online community according to an embodiment of the invention.

Referring now to FIG. 3, an exemplary embodiment of the invention is described. User "BlessedWithMS" has added data to her profile signifying that she has taken the drug PROZAC® (fluoxetine hydrochloride). However, she has neglected to enter other information such as dosage and she has not yet completed an evaluation of the drug to share how she thinks it may or may not have affected her. User "DataJunkie" logs into the online community and views BlessedWithMS's profile, an excerpt 300 of which is depicted in FIG. 3. BlessedWithMS's profile includes a chart 302 displaying the estimated onset 304 and diagnosis 306 of multiple sclerosis and the user's last update 308. Horizontal bar 310 depicts BlessedWithMS's usage history for COPAXONE®. Horizontal bar 312 depicts that BlessedWithMS indicated that she is taking PROZAC®, but did not provide any further usage history.

DataJunkie wants to encourage BlessedWithMS to add the relevant details about PROZAC® and complete an evaluation so as to better inform his decision about whether or not he should take PROZAC® himself. DataJunkie presses the "nudge" button 314 on BlessedWithMS's profile, which prompts DataJunkie to indicate which data fields he is interested in BlessedWithMS completing and why. Once he has indicated the data he is interested in, he transmits the request (e.g., by pressing a "send" button).

Figure 4:
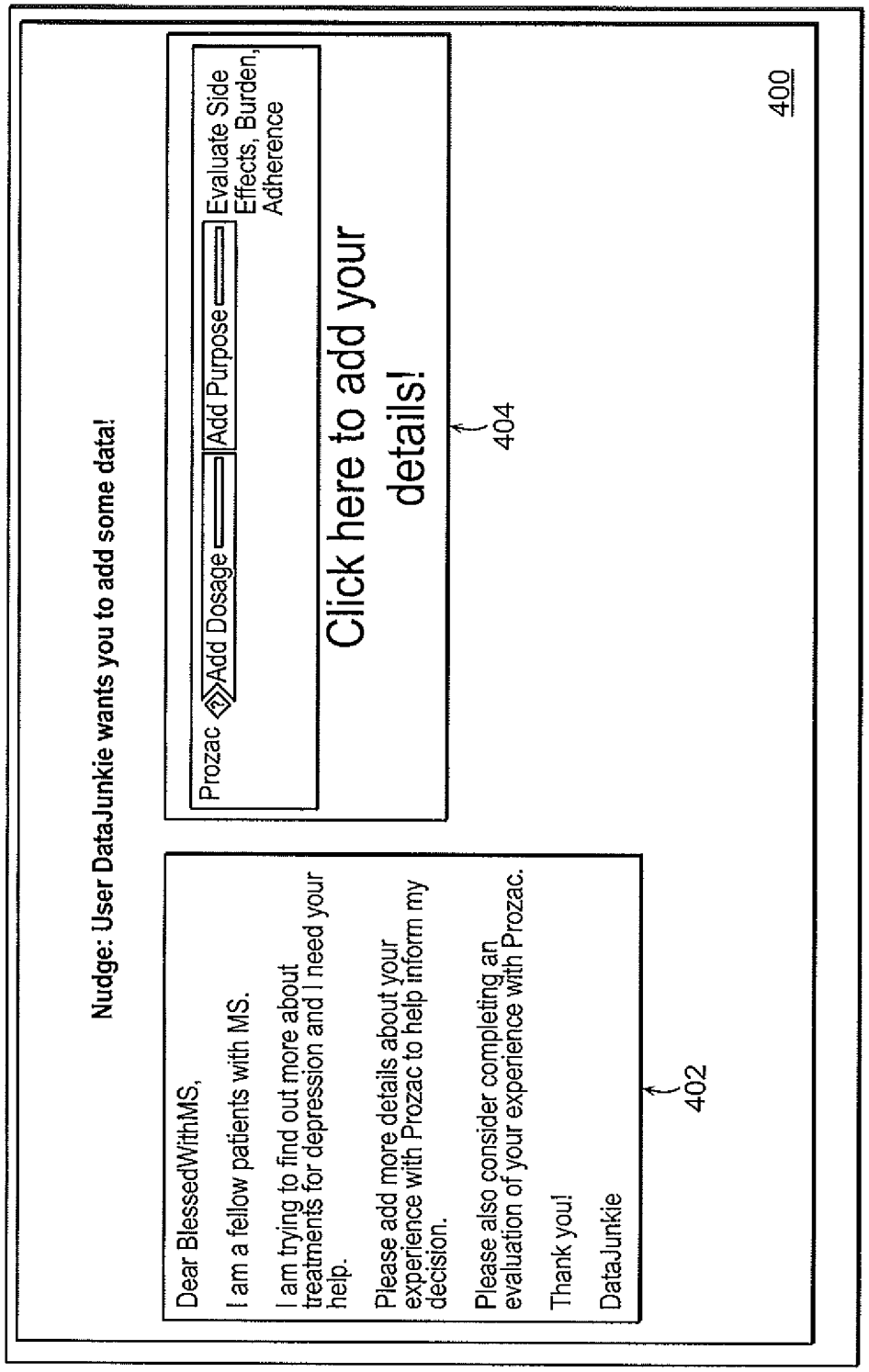
FIG. 4 depicts an exemplary message indicating that another user requests additional information.

User BlessedWithMS receives a message (e.g., a nudge) indicating that another user requests additional information from her. An exemplary message 400 is depicted in FIG. 4. The message 400 can include a component 402 from Data- Junkie and one or more structured data-entry fields 404 that help her provide the relevant information that DataJunkie requested.

In FIG. 5, once BlessedWithMS has entered and transmitted the additional requested data, BlessedWithMS receives an acknowledgment message 500. The acknowledgment message 500 can include a "thank you" message 502 and a report 504 demonstrating how her additional data was pooled to help other users make informed decisions. User DataJunkie is notified that his request has been fulfilled and has the option to send a thank you note.

Referring now to FIG. 6, the additional data can be incorporated with pre-existing user data to create one or more aggregate reports 600. Report 600 can be addressed to specific topics (e.g., specific medical condition or specific remedies). Report 600 includes a description of fluoxetine (PROZAC®) 602, a chart 604 depicting the reasons why users take fluoxetine, and a chart 606 depicting typical dosages. The report 600 also includes a link 608 for users to update their profile, a link 610 to indicate that the post was helpful, and links 612 to profiles of other users taking PROZAC®.

To avoid abuse or annoyance, data requests can be blocked from a named user. Additionally or alternatively, users can set preferences to receive requests only during certain time periods (e.g., amalgamating all requests into a weekly digest), limit requests to certain individuals or groups, or to block requests. Users can also be restricted to send a finite number of requests within a given time period.

Example 2

Consumer Feedback Online Community

In another embodiment, the invention is applied to consumer feedback online communities such as general consumer review sites (e.g., YELP®, available from Yelp! Inc. of San Francisco, Calif.; ANGIE'S LIST®, available from Brownstone Publishing, LLC of Indianapolis, Ind.; and EPINIONS®, available from Shopping.com, Inc. of San Jose, Calif.), hotel review sites (e.g., TRIPADVISOR®, available from TripAdvisor LLC of Needham, Mass.), restaurant review sites (e.g., OPENTABLE®, available from OpenTable, Inc. of San Francisco, Calif.; and ZAGAT®, available from Zagat Survey, LLC of New York, N.Y.), consumer electronics review sites (e.g., CNET®, available from CBS Interactive Inc. of New York, N.Y.), and the like.

Various rating scales exist to measure reviewer satisfaction with a service experience. In addition to discrete scales such as asking whether the service was great/good/fair/poor/awful, numerical scales can be used which ask the reviewer to quantify one or aspects of their service experience, for example, on a 1-10 numerical scale. Rating scales can include customer service, quality, hygiene, convenience, speed, ambience, and overall satisfaction.

A review for a given user can be associated with a particular time. For example, a reviewer may submit a review for a restaurant at a given time point, return to the restaurant for additional visits, and submit reviews about each subsequent visit. This allows for organization according to a timeline that can also reflect dates on which the service provider changed ownership and/or underwent refurbishment.

A consumer review online community can be integrated with other online communities. For example, an online review community can be integrated with a social network services such as FACEBOOK®, available from Facebook, Inc. of Palo Alto, Calif.; GATHER.COM®, available from Gather Inc. of Boston, Mass.; LINKEDIN®, available from LinkedIn Corp. of Mountain View, Calif.; PATIENTS-LIKEME®, available from PatientsLikeMe, Inc. of Cambridge, Mass.; and the like. Under such an arrangement, if a first user is considering dining at a restaurant, the first user could be alerted that a second user in their network recently dined at that restaurant, but has not submitted a review. The first user can then request that the second user complete a review for the restaurant.

Data Verification and Enhancement

In another embodiment, the systems and methods disclosed herein are adapted to facilitate the verification and enhancement of data in an online community.

Users may from time to time enter anomalous data. For example, a first user suffering from amyotrophic lateral sclerosis (ALS) can indicate that she is taking 200 mg of lithium daily. Other users reviewing her profile notice this data and send a message to the first user asking her to verify whether this data is correct. The user can then respond to confirm that the data is correct (at which point, future verification requests for this data point can be disabled) or correct the data. Such a method promotes confidence in the data and can help to identify new remedies.

Users can also enter data on various events (e.g., changes in medical condition). For example, a first user taking lithium for ALS may report that she has developed acne vulgaris. Another user may send a message to the first user inquiring whether the development of acne is an "adverse event" and inquire what the user believes may have caused her acne. Data from the response can be pooled to identify adverse effects caused by remedies and be particularly useful in identifying previously-unknown adverse drug-drug interactions.

Integration of Reward System(s)

The online communities described herein can be integrated with one or more reward systems to encourage increased user participation. For example, users may earn credits (also known as points, stars, and the like) for posting information, sending a request for additional information to another user, responding to a request, and the like. Various systems for awarding credits are described in publications such as U.S. Patent Application Publication No. 2002/0184094.

Credits can be used in a variety of ways. The number of credits earned by the user can be displayed in the user's profile. The user can attain various levels reflecting the user's contribution to the online community. The credits can be redeemable for various prizes. The credits can also be used to affect the display of information in the online community. For example, postings for users with more credits may be displayed more prominently than users with fewer credits.

Identification of Potential Side Effects

Embodiments of the invention can be utilized to identify potential side effects of interventions.

INCORPORATION BY REFERENCE

All patents, published patent applications, and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Specifically, although this application periodically discusses the application of the invention to "diseases", the invention is equally applicable to other medical events such as aging, fertility, and the like. Moreover, the invention is not limited to medical events and conditions, but is applicable to other topics such as athletic training, weight loss, academic performance, financial management, and the like. Such equivalents are intended to be encompassed by the following claims.

The invention claimed is:

1. A method for encouraging active participation in an online community, the method comprising:
    receiving into a database, by a processor, information from a first user regarding a topic;
        wherein the database is accessible by at least one other user in the online community;
    receiving, by the processor, a request from a second user for additional information from the first user;
    determining, by the processor, relevant additional information to the information from the first user based on a data mining of the database;
    generating, by the processor, a personalized message to the first user requesting the relevant additional information; and
    causing to display, by the processor, an information request prompt on a display associated with the first user;
        wherein the information request prompt comprises the personalized message and at least one user selectable data field enabling the first user to specify the relevant additional information.

2. The method of claim 1, further comprising:
    receiving, by the processor, the additional information from the first user.

3. The method of claim 1, further comprising:
    updating, by the processor, the database with the additional information.

4. The method of claim 1, wherein the personalized message includes a component generated by the second user.

5. The method of claim 1, further comprising:
    notifying, by the processor, the second user when the additional information is received.

6. The method of claim 1, further comprising:
    prompting, by the processor, the second user to thank the first user.

7. The method of claim 1, wherein the online community is a topic-related online community.

8. The method of claim 7, wherein the topic relates to health.

9. The method of claim 1, wherein the additional information includes at least one medical condition metric.

10. The method of claim 9, wherein the medical condition metric is a quantitative representation of a medical condition.

11. The method of claim 9, wherein the medical condition metric is one selected from the group consisting of: a direct measure of pathology, a user-reported measure of functional impairment, a user-reported outcome of health-related quality of life, and a user-reported progression of a medical condition.

12. The method of claim 1, wherein the relevant additional information includes intervention data.

13. The method of claim 1, wherein the method is computer-implemented method.

14. The method of claim 1, wherein the relevant additional information includes one or more adverse events.

15. The method of claim 1, wherein the information comprises adverse events comprising one or more selected from the group consisting of side effects, hospitalizations, and monies paid.

16. The method of claim 1, wherein the relevant additional information includes one or more selected from the group consisting of laboratory data, general qualitative data, and diagnostic test data.

17. A non-transitory and tangible computer-readable medium whose contents cause a computer to perform a method for encouraging active participation in an online community, the method comprising:
    receiving, into a database, information from a first user regarding a topic;
        wherein the database is accessible by at least one other user in the online community;
    receiving a request from a second user for additional information from the first user;
    determining relevant additional information to the information from the first user based on a data mining of the database; and
    generating a personalized message to the first user requesting the relevant additional information; and
    causing to display an information request prompt on a display associated with the first user;
        wherein the information request prompt comprises the personalized message and at least one user selectable data field enabling the first user to specify the relevant additional information.

18. A system for encouraging active participation in an online community, the system comprising:
    a server configured to:
        receive, into a database, information from a first user regarding a topic;
            wherein the database is accessible by at least one other user in the online community;
        receive a request from a second user for additional information from the first user;
        determine relevant additional information to the information from the first user based on a data mining of the database; and
        generate a personalized message to the first user requesting the relevant additional information; and
    a first client configured to:
        transmit information from the first user to the server; and
        display an information request prompt comprising the personalized message from the server and at least one user selectable data field enabling the first user to specify the relevant additional information.

19. The system of claim 18, further comprising:
    a second client configured to:
        transmit the request for the additional information to the server; and
        receive a notification that the additional information was provided by the first user.

* * * * *